US00PP29066P3

(12) United States Plant Patent
Barends

(10) Patent No.: US PP29,066 P3
(45) Date of Patent: Mar. 6, 2018

(54) ***PELARGONIUM* PLANT NAMED 'FIPELBROCHENI'**

(50) Latin Name: *Pelargonium×hortorum*
Varietal Denomination: Fipelbrocheni

(71) Applicant: FIDES B.V., De Lier (NL)

(72) Inventor: Eveline Barends, De Lier (NL)

(73) Assignee: Dümmen Group B.V., De Lier (NL)

( * ) Notice: Subject to any disclaimer, the term of this patent is extended or adjusted under 35 U.S.C. 154(b) by 4 days.

(21) Appl. No.: 14/999,893

(22) Filed: Jul. 14, 2016

(65) Prior Publication Data

US 2018/0020597 P1 Jan. 18, 2018

(51) Int. Cl.
*A01H 5/02* (2006.01)

(52) U.S. Cl.
USPC ..... Plt./329

(58) Field of Classification Search
USPC ..... Plt./324, 325, 329
See application file for complete search history.

*Primary Examiner* — Susan McCormick Ewoldt
(74) *Attorney, Agent, or Firm* — C. A. Whealy

(57) ABSTRACT

A new and distinct cultivar of *Pelargonium* plant named 'Fipelbrocheni', characterized by its upright to outwardly spreading and uniformly mounding plant habit; moderately freely basal branching habit; leaves with a prominent dark brown-colored central zonal pattern and green-colored margins; early and freely flowering habit; semi-double cherry red-colored flowers arranged on rounded umbels; and good garden performance.

1 Drawing Sheet

Botanical designation: *Pelargonium×hortorum.*
Cultivar denomination: 'FIPELBROCHENI'.

BACKGROUND OF THE INVENTION

The present invention relates to a new and distinct cultivar of *Pelargonium* plant, botanically known as *Pelargonium×hortorum*, commonly referred to as Zonale Geranium, and hereinafter referred to by the name 'Fipelbrocheni'.

The new *Pelargonium* plant is a product of a planned breeding program conducted by the Inventor in Puerto Lumbreras, Spain and De Lier, The Netherlands. The objective of the breeding program is to create new freely-branching and freely-flowering *Pelargonium* plants with attractive leaf and flower coloration.

The new *Pelargonium* plant originated from a cross-pollination made by the Inventor in July, 2012 in Puerto Lumbreras, Spain of a proprietary selection of *Pelargonium×hortorum* identified as code number 60038, not patented, as the female, or seed, parent with a proprietary selection of *Pelargonium×hortorum* identified as code number 88846, not patented, as the male, or pollen, parent. The new *Pelargonium* plant was discovered and selected by the Inventor as a single flowering plant from within the progeny of the stated cross-pollination in a controlled greenhouse environment in De Lier, The Netherlands in July, 2013.

Asexual reproduction of the new *Pelargonium* plant by vegetative terminal cuttings in a controlled greenhouse environment in De Lier, The Netherlands since August, 2013 has shown that the unique features of this new *Pelargonium* plant are stable and reproduced true to type in successive generations.

SUMMARY OF THE INVENTION

Plants of the new *Pelargonium* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Fipelbrocheni'. These characteristics in combination distinguish 'Fipelbrocheni' as a new and distinct *Pelargonium* plant:

1. Upright to outwardly spreading and uniformly mounding plant habit.
2. Moderately freely basal branching habit.
3. Leaves with a prominent dark brown-colored central zonal pattern and green-colored margins.
4. Early and freely flowering habit.
5. Semi-double cherry red-colored flowers arranged on rounded umbels.
6. Good garden performance.

Plants of the new *Pelargonium* differ primarily from plants of the female parent selection in flower petal color as plants of the female parent selection have red-colored flower petals. In addition, plants of the new *Pelargonium* have semi-double flowers whereas plants of the female parent selection have single-type flowers.

Plants of the new *Pelargonium* differ primarily from plants of the male parent selection in flower petal color as plants of the male parent selection have pink-colored flower petals.

Plants of the new *Pelargonium* can be compared to plants of *Pelargonium×hortorum* 'Mrs. Pollock', not patented. In side-by-side comparisons plants of the new *Pelargonium* differ primarily from plants of 'Mrs. Pollock' in the following characteristics:

1. Plants of the new *Pelargonium* are more freely branching than plants of 'Mrs. Pollock'.
2. Leaves of plants of the new *Pelargonium* are dark brown in color with green-colored margins whereas leaves of plants of 'Mrs. Pollock' are green, brown and yellow in color.

3. Plants of the new *Pelargonium* have larger flowers than plants of 'Mrs. Pollock'.
4. Plants of the new *Pelargonium* have semi-double flowers whereas plants of 'Mrs. Pollock' have single-type flowers.

BRIEF DESCRIPTION OF THE PHOTOGRAPH

The accompanying colored photograph illustrates the overall appearance of the new *Pelargonium* plant showing the colors as true as it is reasonably possible to obtain in colored reproductions of this type. Colors in the photograph may differ slightly from the color values cited in the detailed botanical description which accurately describe the colors of the new *Pelargonium* plant.

The photograph is a side perspective view of a typical flowering plant of 'Fipelbrocheni' grown in a container.

DETAILED BOTANICAL DESCRIPTION

The aforementioned photograph and following observations, measurements and values describe plants grown during the winter and early spring in 12-cm containers in a glass-covered greenhouse in De Lier, The Netherlands and under cultural practices typical of commercial Zonale *Pelargonium* production. During the production of the plants, day temperatures averaged 17° C. and night temperatures averaged 14° C. Plants were 15 weeks old when the photograph and description were taken. In the detailed description, color references are made to The Royal Horticultural Society Colour Chart, 2007 Edition, except where general terms of ordinary dictionary significance are used.

Botanical classification: *Pelargonium×hortorum* 'Fipelbrocheni'.

Parentage:

*Female, or seed, parent*.—Proprietary selection of *Pelargonium×hortorum* identified as code number 60038, not patented.

*Male or pollen parent*.—Proprietary selection of *Pelargonium×hortorum* identified as code number 88846, not patented.

Propagation:

*Type*.—By vegetative terminal cuttings.

*Time to initiate roots, summer and winter*.—About ten days at temperatures about 19° C.

*Time to produce a rooted young plant, summer and winter*.—About 18 days at temperatures about 19° C.

*Root description*.—Medium in thickness, fibrous; typically creamy white in color, actual color of the roots is dependent on substrate composition, water quality, fertilizer type and formulation, substrate temperature and physiological age of roots.

*Rooting habit*.—Moderately freely branching, medium density.

Plant description:

*Plant habit*.—Upright to outwardly spreading and uniformly mounding plant habit; densely foliated.

*Growth and branching habit*.—Moderately vigorous growth habit; moderate growth rate; moderately freely basal branching habit.

*Plant height, to top of floral plane*.—About 22 cm to 24 cm.

*Plant height, to top of foliar plane*.—About 19 cm.

*Plant width*.—About 25 cm.

*Lateral branches*.—Length: About 8.9 cm. Diameter: About 9 mm. Internode length: About 1.8 cm. Strength: Moderately strong. Aspect: Mostly upright. Texture: Pubescent. Color: Close to 145A.

Leaf description:

*Arrangement*.—Alternate; simple.

*Length*.—About 6.3 cm.

*Width*.—About 7.5 cm.

*Shape*.—Reniform.

*Apex*.—Rounded.

*Base*.—Cordate.

*Margin*.—Crenate.

*Venation pattern*.—Palmate.

*Texture, upper surface*.—Pubescent.

*Texture, lower surface*.—Smooth, glabrous.

*Color*.—Developing leaves, upper surface: Close to 143B. Developing leaves, lower surface: Close to 148B. Fully expanded leaves, upper surface: Close to 143D; venation, close to 143D. Fully expanded leaves, lower surface: Close to 147B; venation, close to 145B. Zonation pattern, upper surface only: Location: About 3 mm from the margin edge. Width: About 6 cm. Color: Close to 200A.

*Petioles*.—Length: About 6 cm. Diameter: About 2.7 mm. Texture, upper and lower surfaces: Smooth, glabrous. Color, upper and lower surfaces: Close to 144A.

Flower description:

*Flower arrangement*.—Semi-double round flowers arranged in rounded hemispherical umbels arising from apical leaf axils; umbels displayed above the foliar plane on strong peduncles; flowers face upright to outwardly.

*Fragrance*.—None detected.

*Quantity of flowers*.—Freely flowering habit; about 20 flowers and flower buds per umbel and numerous umbels developing per plant during the flowering season.

*Flowering season*.—In The Netherlands, flowering is continuous from spring through the summer; early flowering habit, plants begin flowering about eight weeks after planting.

*Flower longevity*.—Individual flowers last about five to seven days on the plant; flowers persistent.

*Umbel height*.—About 4.4 cm.

*Umbel diameter*.—About 5.9 cm.

*Flower diameter*.—About 2.7 cm by 3.4 cm.

*Flower depth (height)*.—About 1.2 cm.

*Flower buds*.—Length: About 1.4 cm. Diameter: About 5.9 mm. Shape: Ovoid. Color: Close to 64A.

*Petals*.—Quantity per flower: About five to seven. Length: About 2 cm. Width: About 1.5 cm. Shape: Obovate. Apex: Round. Base: Attenuate. Margin: Sinuate. Texture, upper and lower surfaces: Smooth, glabrous. Color: When opening, upper surface: Close to N66A. When opening, lower surface: Close to N66C. Fully opened, upper surface: Close to 50A; venation, close to N66A. Fully opened, lower surface: Close to N66C; venation, close to N66C.

*Petaloids*.—Quantity per flower: About three to five. Length: About 6 mm. Width: About 3 mm. Shape: Obovate. Apex: Round. Base: Attenuate. Margin: Sinuate. Texture, upper and lower surfaces: Smooth, glabrous. Color: When opening and fully opened, upper surface; Close to N66A. When opening and fully opened, lower surface: Close to N66C.

*Sepals*.—Quantity per flower: Ten arranged in one to two whorls. Length: About 5.5 mm. Width: About 3 mm. Shape: Ensiform. Apex: Acuminate. Base: Acute. Margin: Entire. Texture, upper and lower surfaces: Smooth, glabrous. Color, upper and lower surfaces: Close to 144A.

*Peduncle* (*umbel stem*).—Length: About 12.3 cm. Diameter: About 3.9 mm. Strength: Moderately strong. Aspect: Mostly upright. Texture: Smooth, glabrous. Color: Close to 144B.

*Pedicel* (*individual flower stem*).—Length: About 1.1 cm. Diameter: About 1 mm. Strength: Moderately strong. Angle: Mostly upright. Texture: Smooth, glabous. Color: Close to 144B.

*Reproductive organs*.—Androecium: Stamen quantity per flower: About four. Filament length: About 6.4 mm. Filament color: Close to 36A. Anther length: About 1.1 cm. Anther shape: Oblong. Anther color: Close to 150D. Pollen amount: Moderate. Pollen color: Close to 28A. Gynoecium: Pistil quantity per flower: One. Pistil length: About 6 mm. Stigma shape: Decurrent. Stigma color: Close to 38A. Style length: About 1.2 mm. Style color: Close to 38A. Ovary color: Close to 144A.

*Fruits and seeds*.—Fruit and seed development has not been observed on plants of the new *Pelargonium*.

Disease & pest resistance: Plants of the new *Pelargonium* have not been observed to be resistant to pathogens and pests common to *Pelargonium* plants.

Garden performance: Plants of the new *Pelargonium* have been observed to have good garden performance and to tolerate rain, wind and temperatures ranging from about 5° C. to 45° C.

It is claimed:

1. A new and distinct *Pelargonium* plant named 'Fipelbrocheni' as illustrated and described.

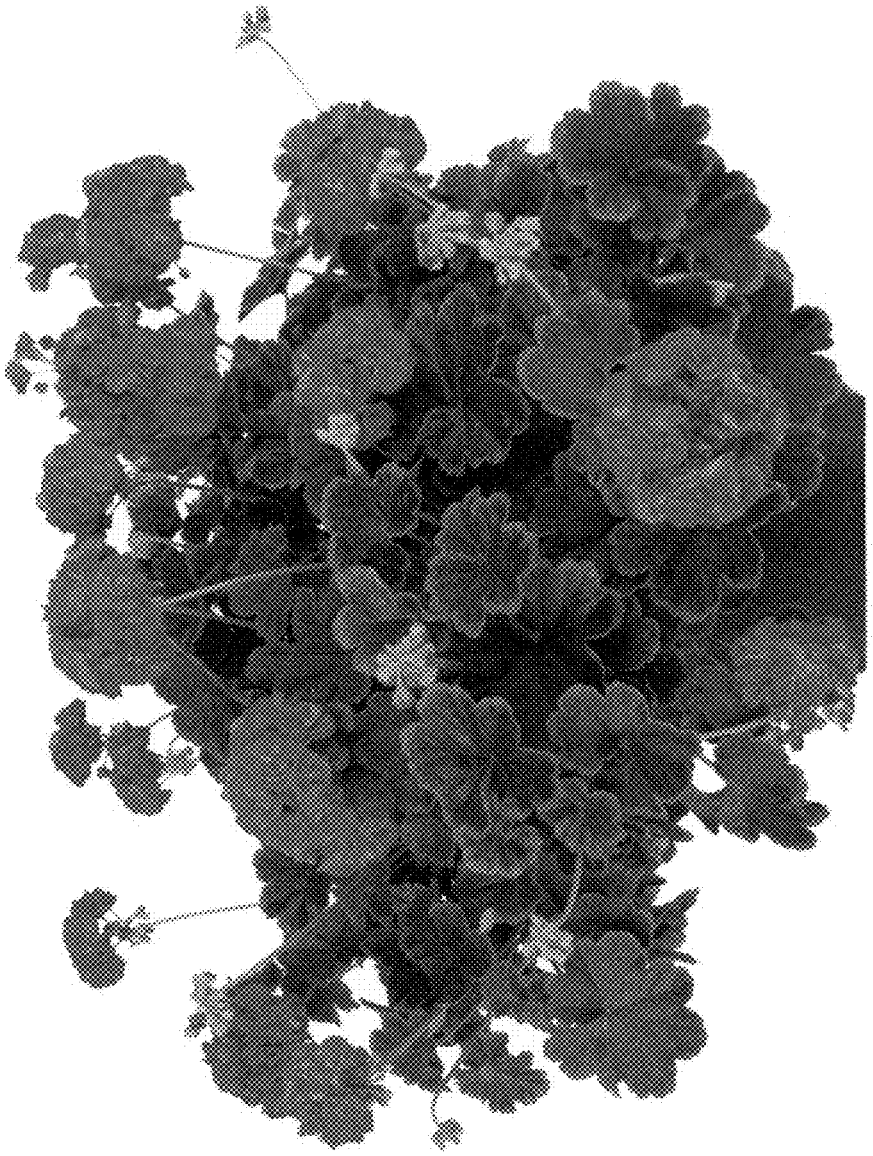

* * * * *